United States Patent [19]
Tanner et al.

[11] Patent Number: 5,989,528
[45] Date of Patent: Nov. 23, 1999

[54] SUNSCREEN COMPOSITIONS

[75] Inventors: Paul Robert Tanner, Maineville; Christopher Irwin, Cincinnati; Margaret Ann O'Donoghue, Monroe, all of Ohio

[73] Assignee: The Procter & Gamble Company, Cincinnati, Ohio

[21] Appl. No.: 09/126,486

[22] Filed: Jul. 30, 1998

[51] Int. Cl.[6] .............. A61K 7/42; A61K 7/44; A61K 7/00
[52] U.S. Cl. .............. 424/59; 424/60; 424/400; 424/401
[58] Field of Search .............. 424/59, 60, 400, 424/401

[56] References Cited

U.S. PATENT DOCUMENTS

| | | | |
|---|---|---|---|
| 5,152,983 | 10/1992 | Nambudiry et al. | 424/60 |
| 5,538,416 | 7/1996 | Forestier et al. | 424/59 |
| 5,549,886 | 8/1996 | Grollier | 424/59 |
| 5,567,418 | 10/1996 | Forestier et al. | 424/59 |
| 5,576,354 | 11/1996 | Deflandre et al. | 514/685 |
| 5,587,150 | 12/1996 | Deflandre et al. | 424/59 |
| 5,605,680 | 2/1997 | Deflandre et al. | 424/59 |
| 5,618,520 | 4/1997 | Hansenne et al. | 424/59 |
| 5,620,682 | 4/1997 | Fogel | 424/60 |
| 5,624,663 | 4/1997 | Deflandre et al. | 424/59 |
| 5,672,337 | 9/1997 | Ascione | 424/59 |
| 5,783,174 | 7/1998 | Deckner | 424/59 |

FOREIGN PATENT DOCUMENTS

| | | |
|---|---|---|
| 0 709 080 A1 | 5/1996 | European Pat. Off. . |
| 0 717 982 A1 | 6/1996 | European Pat. Off. . |
| 0 754 445 A2 | 1/1997 | European Pat. Off. . |
| 0 780 119 A1 | 6/1997 | European Pat. Off. . |
| 0 787 483 A1 | 8/1997 | European Pat. Off. . |
| 2 198 944 | 6/1988 | United Kingdom . |
| 97/21422 | 6/1997 | WIPO . |

*Primary Examiner*—Shelley A. Dodson
*Attorney, Agent, or Firm*—Dara M. Kendall; Loretta J. Henderson

[57] ABSTRACT

The present invention relates to compositions suitable for use as sunscreens which provide excellent stability, efficiency, and UV protection efficacy in a safe, economical and aesthetically appealing manner (on-skin transparency, low skin irritation). Methods of use for these compositions are also disclosed. The compositions comprise:

a) a safe and effective amount of a UVA-absorbing dibenzoylmethane sunscreen active;

b) a safe and effective amount of a stabilizing agent having the formula

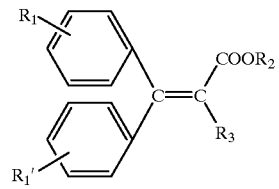

wherein $R_1$ and $R_1'$ are independently in the para or meta position and are independently a hydrogen atom or a straight- or branched chain $C_1$–$C_8$ alkyl radical, $R_2$ is a straight- or branched-chain $C_1$–$C_{12}$ alkyl radical; and $R_3$ is a hydrogen atom or a —CN radical;

c) a safe and effective amount of a UVB sunscreen selected from the group consisting of organic sunscreen actives, inorganic physical sunblocks, and mixtures thereof, wherein the inorganic physical sunblock is present in a total amount of less than or equal to about 5%; and d) a carrier suitable for application to the skin wherein the mole ratio of the stabilizing agent to the UVA-absorbing dibenzoylmethane sunscreen active is less than 0.8 and wherein the composition is substantially free of benzylidene camphor derivatives.

19 Claims, No Drawings

5,989,528

SUNSCREEN COMPOSITIONS

TECHNICAL FIELD

The present invention relates to compositions suitable for use as sunscreens having excellent efficiency, broad spectrum UV efficacy, photostability and transparency on the skin. The compositions comprise a UVA-absorbing dibenzoylmethane sunscreen active, a stabilizing agent, a UVB sunscreen active, and a carrier suitable for application to the skin, and are substantially free of benzylidene camphor derivatives.

BACKGROUND OF THE INVENTION

It is well known that exposure to sunlight can pose a number of hazards to the skin. These damaging effects may result not only from sunbathing but also from the sunlight exposure associated with daily outdoor activities. The major short term hazard of prolonged exposure to sunlight is erythema, i.e. sunburn, which primarily results from UVB radiation having a wavelength of from about 290 nm to about 320 nm. Over the long term, however, malignant changes in the skin surface often occur. Numerous epidemiologic studies demonstrate a strong relationship between sunlight exposure and human skin cancer. Another long term hazard of ultraviolet radiation is premature aging of the skin, which is primarily caused by UVA radiation having a wavelength of from about 320 nm to about 400 nm. This condition is characterized by wrinkling and pigment changes of the skin, along with other physical changes such as cracking, telangiectasis, solar dermatoses, ecchymoses, and loss of elasticity. The adverse effects associated with exposure to UV radiation are more fully discussed in DeSimone, "Sunscreen and Suntan Products," *Handbook of Nonprescription Drugs*, 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation," *International Journal of Cosmetic Science*, 4, pp. 15–24 (1982); and U.S. Pat. No. 4,387,089, DePolo, issued Jun. 7, 1983.

As a result of the abovementioned hazards associated with sunlight exposure, the general public's interest in the sun protection product market has grown considerably. Today, there are not only sunscreen products for sunbathing but there are also a variety of personal care products containing sunscreens, particularly cosmetic type products which are worn daily. "Personal care products" refer to health and cosmetic beauty aid products generally recognized as being formulated for beautifying and grooming the skin and hair. For example, personal care products include sunscreen products (e.g., lotions, skin creams, etc.), cosmetics, toiletries, and over-the-counter pharmaceutical products intended for topical usage.

Not surprisingly, consumers desire that sunscreen products, particularly daily wear products, be effective, aesthetically pleasing to their senses of sight and feel, and economical. Unfortunately, most commercially available sunscreen products are lacking in one or more of these areas.

For example, most commercial sunscreens utilize high levels of sunscreen actives in order to achieve desired levels of UV protection. These high levels of sunscreen actives not only increase the cost of the product but also tend to contribute to poor aesthetics (e.g., poor skin feel, skin whitening, etc.) and skin irritation.

Many conventional sunscreen products are also deficient due to their inability to provide efficacious protection against broad spectrum UV radiation, i.e., protection against both UVB and UVA radiation. Today, most commercially available sunscreen products are efficient at absorbing UV radiation in the 290 nm to 320 nm UVB region such that sunburn of the skin is prevented. They are less efficient when it comes to absorbing light which falls in the 320 nm to 400 nm UVA region, which leaves the skin vulnerable to premature skin aging. This deficiency is due in part to the limited number of UVA absorbing sunscreen actives which are both commercially available and approved for global use.

A wide variety of sunscreen actives have been used in personal care products. It is desirable that the sunscreen active or active system provide broad spectrum UV protection, particularly protection against both UVA radiation and UVB radiation. In addition, the active should be approved for human use, preferably on a global basis. It is further desirable that these sunscreen actives are easily formulated to provide stable, efficacious, and aesthetically appealing sunscreen products.

Dibenzoylmethane compounds are one class of sunscreen compounds which provide broad spectrum UV protection and are approved for global use. Unfortunately, these sunscreens tend to photodegrade upon exposure to UV radiation thereby reducing their UVA efficacy. One approach to stabilize these types of sunscreens is described in U.S. Ser. No. 07/929,612, Deckner, filed Aug. 13, 1992, involving the use of benzylidene camphor sunscreens to stabilize the dibenzoylmethane compound. Such compositions, however, are not currently approved for global use.

Another class of sunscreen actives known as physical sunblocks have also been used to provide protection to the skin against broad spectrum UV radiation. Physical sunblocks are inorganic compounds which are believed to exert their effects by scattering, reflecting or absorbing UV radiation. See, Sayre, R. M. et al., "Physical Sunscreens," *J. Soc. Cosmet. Chem.*, vol. 41, no. 2, pp. 103–109 (1990). Unfortunately, when used at effective levels, such sunscreen actives tend to leave an undesirable white film on the consumer's skin and/or agglomerate in the finished product.

A need therefore remains for stable (including photostable), efficient sunscreen products which provide broad spectrum UV protection (i.e., against both UVA and UVB radiation) in a safe, economical, and aesthetically appealing manner (on-skin transparency and low skin irritation).

It has surprisingly now been found that the compositions of the present invention, which comprise a UVA-absorbing dibenzoylmethane sunscreen active, a defined stabilizing agent, a UVB sunscreen active, and a carrier, and which are substantially free of benzylidene camphor derivatives, provide excellent stability (especially photostability), efficiency, and UV protection efficacy (including both UVA and UVB protection), in a safe, economical and aesthetically appealing (particularly on-skin transparency and without undue skin irritation) manner.

SUMMARY OF THE INVENTION

The present invention relates to a composition suitable for use as sunscreen comprising:

a) a safe and effective amount of a UVA-absorbing dibenzoylmethane sunscreen active;

b) a safe and effective amount of a stabilizing agent having the formula

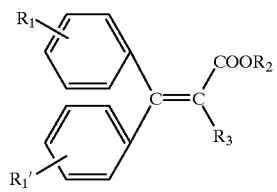

wherein $R_1$ and $R_1'$ are independently in the para or meta position and are independently a hydrogen atom or a straight- or branched chain $C_1$–$C_8$ alkyl radical, $R_2$ is a straight- or branched-chain $C_1$–$C_{12}$ alkyl radical; and $R_3$ is a hydrogen atom or a —CN radical; and c) a safe and effective amount of a UVB sunscreen active selected from the group consisting of organic sunscreen actives, inorganic physical sunblocks, and mixtures thereof, wherein any inorganic physical sunblock is present in a total amount of less than or equal to about 5%; and d) a carrier suitable for application to the skin;

wherein the mole ratio of the stabilizing agent to the UVA-absorbing sunscreen active is less than 0.8 and the composition is substantially free of benzylidene camphor derivatives. In preferred embodiments, the mole ratio of the stabilizing agent to the UVA-absorbing dibenzoylmethane sunscreen active is less than about 0.75, more preferably less than about 0.70, and most preferably less than about 0.65. The present invention also relates to methods for providing protection to human skin from the harmful effects of UV radiation by topical application of such compositions.

DETAILED DESCRIPTION OF THE INVENTION

The compositions of the present invention are useful for providing protection to human skin against the harmful effects of ultraviolet radiation. The essential components of these compositions are described below. Also included is a nonexclusive description of various optional and preferred components useful in embodiments of the present invention.

The present invention can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All molar weights are weight average molecular weights and are given in units of grams per mole.

All ingredient levels are in reference to the active level of that ingredient, and are exclusive of solvents, by-products, or other impurities that may be present in commercially available sources, unless otherwise indicated.

All measurements made are at ambient room temperature, which is approximately 73° F., unless otherwise designated.

All documents referred to herein, including patents, patent applications, and printed publications, are hereby incorporated by reference in their entirety in this disclosure.

By "safe and effective amount" is meant an amount of a compound, component, or composition (as applicable) sufficient to significantly induce a positive effect (e.g., photoprotection or stability), but low enough to avoid serious side effects, (e.g., undue toxicity or allergic reaction), i.e., to provide a reasonable benefit to risk ratio, within the scope of sound medical judgment.

UVA-Absorbing Dibenzoylmethane Sunscreen Active

The compositions of the present invention comprise a UVA-absorbing dibenzoylmethane sunscreen active which absorbs UV radiation having a wavelength of from about 320 nm to about 400 nm. Examples of such dibenzoylmethane sunscreen actives are described in U.S. Pat. No. 4,489,057, issued to Welters et al. on Dec. 18, 1984 and U.S. Pat. No. 4,387,089, issued to Depolo on Jun. 7, 1983; and in *Sunscreens: Development, Evaluation, and Regulatory Aspects,* edited by N. J. Lowe and N. A. Shaath, Marcel Dekker, Inc. (1990).

Suitable dibenzoylmethane sunscreen actives include, but are not limited to, those selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4'tert-butyl-4'methoxydibenzoylmethane, and mixtures thereof. Preferred dibenzoylmethane sunscreen actives include those selected from the group consisting of 4-(1,1-dimethylethyl)-4'methoxydibenzoylmethane, isopropyldibenzoylmethane, and mixtures thereof. A more preferred dibenzoylmethane sunscreen active is 4-(1,1-dimethylethyl)-4'methoxydibenzoylmethane.

The sunscreen active, 4-(1,1-dimethylethyl)-4'methoxydibenzoylmethane, which is also known as butyl methoxydibenzoylmethane or Avobenzone, is commercially available under the names Parsol® 1789 from Givaudan-Roure (International) S. A. (Basel, Switzerland) and Eusolex® 9020 from Merck & Co., Inc. (Whitehouse Station, N.J.). The sunscreen 4-isopropyldibenzoylmethane, which is also known as isopropyl dibenzoylmethane, is commercially available from Merck under the name Eusolex® 8020.

The UVA-absorbing dibenzoylmethane sunscreen active of the instant invention is present in a safe and effective amount to provide broad spectrum UV protection either independently or in combination with other UV protective actives which may be present in the composition. The composition preferably contains from about 0.1% to about 10%, more preferably from about 0.2% to about 7%, and most preferably from about 0.4% to about 5%. Exact amounts of the sunscreen active will vary depending upon the desired Sun Protection Factor, i.e. the "SPF" of the composition as well as the desired level of UVA protection. (SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. See *Federal Register,* 43, No. 166, pp. 38206–38269, Aug. 25, 1978).

Stabilizing Agent

The compositions of the present invention also comprise a stabilizing agent having the formula

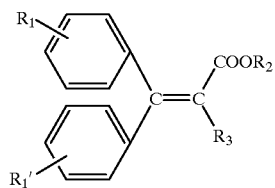

wherein $R_1$ and $R_1'$ are independently in the para or meta position and are independently a hydrogen atom or a straight- or branched chain $C_1$–$C_8$ alkyl radical, $R_2$ is a straight- or branched-chain $C_1$–$C_{12}$ alkyl radical; and $R_3$ is a hydrogen atom or a —CN radical wherein the mole ratio of the stabilizing agent to the UVA-absorbing dibenzoylmethane sunscreen active is less than 0.8, preferably less than about 0.75, more preferably less than about 0.7, and most preferably less than about 0.65. Suitable stabilizing agents are commercially available from Haarman & Reimer, S. A. (Mexico) and are described in U.S. Pat. Nos. 3,215,724 and 5,587,150. Preferred stabilizing agents are selected from the group consisting of 2-ethylhexyl-2-cyano-3,3-diphenylacrylate (referred to as octocrylene), ethyl-2-cyano-3,3-diphenylacrylate, 2-ethylhexyl-3,3-diphenylacrylate, ethyl-3,3-bis(4-methoxyphenyl)acrylate, and mixtures thereof. 2-ethylhexyl-2-cyano-3,3-diphenylacrylate is more preferred.

The stabilizing agent of the present invention is present in a safe and effective amount to reduce photodegradation of the dibenzoylmethane compound. Photodegradation may be determined by a reduction of UV absorbance capability which in turn may be measured by using standard UV absorbance methods. Preferred compositions retain at least about 85%, more preferably at least about 90%, of their initial UV absorbance after irradiation with approximately 2 J/cm² per desired SPF unit of broad band UV radiation, e.g., 30 J/cm² for an SPF 15 composition. The stabilizing agent is preferably used in an amount of from about 0.1% to about 6%, more preferably from about 0.3% to about 3%, and most preferably from about 1.5% to about 2.25%.

UVB Sunscreen Active

The compositions of the present invention further comprise a UVB sunscreen active which absorbs UV radiation having a wavelength of from about 290 nm to about 320 nm. As used herein the UVB sunscreen active means an active other than the dibenzoylmethane sunscreen active which itself may possess UVB absorption properties. The compositions comprise an amount of the UVB sunscreen active which is safe and effective to provide UVB protection either independently or in combination with other UV protective actives which may be present in the composition, preferably from about 0.1 % to about 10%, more preferably from about 0.1% to about 4%, and most preferably from about 0.5% to about 2.5% by weight of the composition.

A wide variety of UVB sunscreen actives, including both organic sunscreen actives and inorganic physical sunblocks, are suitable for use herein. Nonlimiting examples of such sunscreen actives are described in U.S. Pat. No. 5,087,445 issued Feb. 11, 1992 to Haffey et al.; and U.S. Pat. Nos. 5,073,371 and 5,073,372, both issued on Dec. 17, 1991 to Turner et al.. Nonlimiting examples of suitable physical sunblocks are described in CTFA International Cosmetic Ingredient Dictionary, Sixth Edition, 1995, pp. 1026–28 and 1103.

Preferred UVB sunscreen actives are selected from the group consisting of 2-phenyl-benzimidazole-5-sulfonic acid, TEA salicylate, octyl dimethyl PABA, zinc oxide, titanium dioxide, and mixtures thereof. A preferred organic sunscreen active is 2-phenyl-benzimidazole-5-sulfonic acid while preferred inorganic physical sunblocks are zinc oxide, titanium dioxide, and mixtures thereof. Salt and acid-neutralized forms of the acidic sunscreens are also useful herein.

When used, the physical sunblocks are present in an amount such that the present compositions are transparent on the skin (i.e., non-whitening), preferably less than or equal to about 5%. When titanium dioxide is used, it can have an anatase, rutile, or amorphous structure. Physical sunblock particles, e.g., titanium dioxide and zinc oxide, can be uncoated or coated with a variety of materials including, but not limited to, amino acids; aluminum compounds such as alumina, aluminum stearate, aluminum laurate, and the like; carboxylic acids and their salts, e.g., stearic acid and its salts; phospholipids such as lecithin; organic silicone compounds; inorganic silicone compounds such as silica and silicates; and mixtures thereof. A preferred titanium dioxide is commercially available from Tayca (Japan) and is distributed by Tri-K Industries (Emerson, N.J.) under the MT micronized series (e.g., MT 100SAS).

Carrier

The compositions of the present invention comprise a carrier, or vehicle, suitable for application to human skin. As used herein a "carrier suitable for application to human skin," means that the carrier and its components are suitable for use in contact with human skin without undue toxicity, incompatibility, instability, allergic response, and the like within the scope of sound medical or formulator's judgment. Such carriers are well-known to one of ordinary skill in the art, and can include one or more compatible liquid or solid filler diluents or vehicles which are suitable for application to human skin. The carrier may comprise one or more active or inactive materials, including but not limited to optional components described below. The carrier comprises the balance of the composition. The compositions of the present invention preferably comprise from about 74% to about 99.7%, more preferably from about 79% to about 99%, carrier by weight of the composition.

The carrier can be formulated in a number of ways, including but not limited to emulsions (in emulsion technology, a composition comprising a "dispersed phase" and a "continuous phase;" the dispersed phase existing as small particles or droplets that are suspended in and surrounded by a continuous phase). For example, suitable emulsions include oil-in-water, water-in-oil, water-in-oil-in-water, oil-in-water-in-oil, and oil-in-water-in-silicone emulsions. Preferred compositions comprise an oil-in-water emulsion.

The compositions of the present invention can be formulated into a wide variety of product types, including creams, lotions, milks, mousses, gels, oils, tonics, and sprays. Preferred compositions are formulated into lotions, creams, gels, and sprays. These product forms may be used for a number of applications, including, but not limited to, hand and body lotions, cold creams, facial moisturizers, anti-acne preparations, topical analgesics, make-ups including foundations and lipsticks, and the like. Any additional components required to formulate such products vary with product type and can be routinely chosen by one skilled in the art.

If compositions of the present invention are formulated as an aerosol and applied to the skin as a spray-on product, a propellant is added to the composition. Examples of suitable propellants include chlorofluorinated lower molecular weight hydrocarbons. A more complete disclosure of propellants useful herein can be found in Sagarin, Cosmetics Science and Technology, 2nd Edition, Vol. 2, pp. 443–465 (1972).

Optional Components

The compositions of the present invention may contain a variety of other ingredients such as are conventionally used in a given product type provided that they do not unacceptably alter the benefits of the invention. These optional components should be suitable for application to human skin, that is, when incorporated into the composition they are suitable for use in contact with human skin without undue toxicity, incompatibility, instability, allergic response, and the like within the scope of sound medical or formulator's judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, erythromycin, zinc, etc.), anti-caking agents, antifoaming agents, additional antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skin bleaching agents (or lightening agents) (e.g., hydroquinone, kojic acid, ascorbic acid, magnesium ascorbyl phosphate, ascorbyl glucosamine), skin-conditioning agents (humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents including agents for preventing, retarding, arresting, and/or reversing skin wrinkles (e.g., alpha-hydroxy acids such as lactic acid and glycolic acid and beta-hydroxy acids such as salicylic acid), thickeners, and vitamins and derivatives thereof (e.g. tocopherol, tocopherol acetate, beta carotene, retinoic acid, retinol, retinoids, retinyl palmitate, niacin, niacinamide, and the like).

The compositions of the present invention may contain one or more of such optional components. Preferred compositions optionally contain one or more materials selected from anti-acne actives, artificial tanning agents, humectants, moisturizers, skin conditioners, and thickening/structuring agents.

a) Anti-Acne Actives

The compositions of the present invention may comprise one or more anti-acne actives. Examples of useful anti-acne actives are described in further detail in U.S. Pat. No. 5,607,980, issued to McAtee et al., on Mar. 4, 1997.

b) Artificial Tanning Agents

The compositions of the present invention may comprise one or more artificial tanning agents. Suitable tanning agents include dihydroxyacetone, tyrosine, and tyrosine esters. See *The Merck Index*, Tenth Edition, entry 3167, p. 463 (1983), and "Dihydroxyacetone for Cosmetics", E. Merck Technical Bulletin, 03-304 110, 319 897, 180 588.

c) Structuring Agent

The compositions of the present invention may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. For example, the structuring agent tends to assist in the formation of the liquid crystalline gel network structures. The structuring agent may also function as an emulsifier or surfactant. Preferred compositions of this invention comprise from about 0.5% to about 20%, more preferably from about 1% to about 10%, most preferably from about 1% to about 5%, of one or more structuring agents.

The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, steareth-21, and mixtures thereof.

d) Thickening Agent (Including Thickeners and Gelling Agents)

The compositions of the present invention can comprise one or more thickening agents, preferably from about 0.1% to about 5%, more preferably from about 0.1% to about 3%, and most preferably from about 0.25% to about 2%, by weight of the composition.

Nonlimiting classes of thickening agents include those selected from the group consisting of:

(i) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; and in *CTFA International Cosmetic Ingredient Dictionary*, Fourth Edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from the group consisting of carbomers, acrylates/$C_{10}$–$C_{30}$ alkyl acrylate crosspolymers, and mixtures thereof.

(ii) Crosslinked Polyacrylate Polymers

The compositions of the present invention can optionally comprise crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987.

(iii) Polyacrylamide Polymers

The compositions of the present invention can optionally comprise polyacrylamide polymers, especially nonionic polyacrylamide polymers including substituted branched or unbranched polymers. Most preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

(iv) Polysaccharides

A wide variety of polysaccharides are useful herein. "Polysaccharides" refer to gelling agents which contain a backbone of repeating sugar (i.e. carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$–$C_{30}$ straight chain or branched chain alkyl group through an ether linkage. Typically these polymers are ethers of $C_{10}$–$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans comprising a linear chain of (1–3) linked glucose units with a (1–6) linked glucose every three units, a commercially available example of which is Clearogel™ CS11 from Michel Mercier Products Inc. (Mountainside, N.J.).

(v) Gums

Other thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Preferred compositions of the present invention include a thickening agent selected from the group consisting of carboxylic acid polymers, crosslinked polyacrylate polymers, polyacrylamide polymers, and mixtures thereof, more preferably selected from the group consisting of carboxylic acid polymers, polyacrylamide polymers, and mixtures thereof.

e) Humectants, Moisturizers, and Skin Conditioners

Preferred compositions optionally comprise one or more humectants, moisturizers, or skin conditioners. A variety of these materials can be employed and each can be present at a level of from about 0.01% to about 20%, more preferably from about 0.1% to about 10%, and most preferably from about 0.5% to about 7%. These materials include, but are not limited to, guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also useful herein are the propoxylated glycerols described in U.S. Pat. No. 4,976,953, to Orr et al., issued Dec. 11, 1990.

Also useful are various $C_1$–$C_{30}$ monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977; U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

f) Emulsifiers

The compositions of the present invention can comprise one or more emulsifiers, e.g., to reduce the interfacial tension between phases and improve the formulation and stability of an emulsion. Suitable emulsifiers include a wide variety of nonionic, cationic, anionic, and zwitterionic emulsifiers. See McCutcheon's, *Detergents and Emulsifiers,* North American Edition (1986), published by Allured Publishing Corporation; U.S. Pat. No. 5,011,681 issued to Ciotti et al. on Apr. 30, 1991; U.S. Pat. No. 4,421,769 issued to Dixon et al. on Dec. 20, 1983; and U.S. Pat. No. 3,755,560 issued to Dickert et al. on Aug. 28, 1973.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers include, but are not limited to, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof. Preferred emulsifiers are steareth-2, steareth-21, TEA stearate, diethanolamine cetyl phosphate, potassium cetyl phosphate, and mixtures thereof. The emulsifier can be used individually or as a mixture of two or more and comprises from about 0.1% to about 10%, more preferably from about 0.15% to about 7%, and most preferably from about 0.25% to about 5% of the compositions of the present invention.

While a variety of optional components may be included in the present compositions, the compositions are substantially free of benzylidene camphor derivatives. As used herein, "substantially free of benzylidene camphor" means the present compositions comprise less than about 0.1% of benzylidene camphor. Preferred compositions comprise less than about 0.05% of benzylidene camphor. Most preferably, the compositions are essentially free of benzylidene camphor, i.e., they contain no detectable benzylidene camphor.

Methods For Protecting The Skin From UV Radiation

The compositions of the present invention are suitable for use as a sunscreen to provide protection to human skin from the harmful effects of UV radiation which include, but are not limited to, sunburn and premature aging of the skin. The present invention therefore also further relates to methods of protecting human skin from the harmful effects of UV radiation. Such methods generally involve attenuating or reducing the amount of UV radiation which reaches the skin's surface. To protect the skin from UV radiation, a safe and effective (photoprotective) amount of the composition is topically applied to the skin. "Topical application" refers to application of the present compositions by spreading, spraying, etc. onto the surface of the skin. The exact amount applied may vary depending on the level of UV protection desired. From about 0.5 mg of composition per cm$^2$ of skin to about 25 mg of composition per cm$^2$ of skin are typically applied.

EXAMPLES

The following examples further describe and demonstrate embodiments within the scope of the present invention. The examples are given solely for the purpose of illustration and are not to be construed as limitations on the present invention, as many variations thereof are possible without departing from the spirit and scope of the invention.

The following sunscreen products are representative of the present invention.

| | Wt % | |
|---|---|---|
| Component | Example I | Example II |
| Butyl Methoxydibenzoylmethane | 2.0 | 3.0 |
| Octocrylene | 1.5 | 2.25 |
| Phenylbenzimidazole Sulfonic Acid | 1.5 | 1.0 |
| Isopropyl Palmitate | 8.0 | 15.0 |
| Butylene Glycol | 2.0 | 2.0 |
| Triethanolamine | 1.6 | 1.3 |
| Glycerin | 1.0 | 1.0 |
| Stearic Acid | 1.0 | 1.0 |
| Cetyl Alcohol | 0.75 | 0.75 |
| DEA Cetyl Phosphate | 0.75 | 0.75 |
| PVP Eicosene Copolymer | 0.5 | 0.5 |
| Stearyl Alcohol | 0.25 | 0.25 |
| Methylparaben | 0.25 | 0.25 |
| Carbomer 954 | 0.2 | 0.2 |
| Propylparaben | 0.15 | 0.15 |
| Acrylates/C$_{10}$–C$_{30}$ Alkyl Acrylate Crosspolymer | 0.125 | 0.125 |
| Disodium EDTA | 0.1 | 0.1 |
| Water | q.s. | q.s. |

Prepare a water phase by mixing in a suitable vessel, the Carbomer 954 and the acrylates/C$_{10}$–C$_{30}$ alkyl acrylates crosspolymer in all but 4% of the water. Add the butylene glycol, glycerin, disodium EDTA, and methylparaben to the water phase and heat to 80° C. Prepare an oil phase in a separate vessel by mixing the isopropyl palmitate, butyl methoxydibenzoylmethane, octocrylene, propylparaben, DEA cetyl phosphate, stearic acid, cetyl alcohol, stearyl alcohol, and PVP eiscosene copolymer and heating to 80° C.

When both phases reach 80° C., slowly add the oil phase to the water phase while milling the system to form an emulsion. Cool the system under agitation. Once the system reaches 70° C., add a premix containing 0.73% of the triethanolamine and 1% of the water to the batch. When the batch cools to about 45° C., add a premix containing the phenylbenzimidazole sulfonic acid, remaining triethanolamine, and remaining water to the batch, cool to about 30° C. and pour into suitable containers.

What is claimed is:

1. A composition suitable for use as sunscreen comprising:
   a) a safe and effective amount of a UVA-absorbing dibenzoylmethane sunscreen active;
   b) a safe and effective amount of a stabilizing agent having the formula

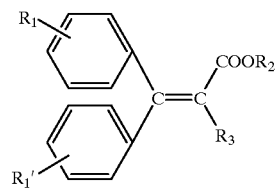

wherein R$_1$ and R$_1$' are independently in the para or meta position and are independently a hydrogen atom or a straight- or branched chain C$_1$–C$_8$ alkyl radical, R$_2$ is a straight- or branched-chain C$_1$–C$_{12}$ alkyl radical; and R$_3$ is a hydrogen atom or a —CN radical;
   c) a safe and effective amount of a UVB sunscreen active selected from the group consisting of organic sunscreen actives, inorganic physical sunblocks, and mixtures thereof selected from the group consisting of 2-phenyl-benzimidazole-5-sulfonic acid, TEA salicylate, octyl dimethyl PABA, zinc oxide, titanium dioxide, and mixtures thereof provided that the composition comprises less than or equal to about 5% inorganic physical sunblock; and d) a carrier suitable for application to the skin;

wherein the mole ratio of the stabilizing agent to the UVA-absorbing dibenzoylmethane sunscreen active is less than 0.8 and wherein the composition is substantially free of benzylidene camphor derivatives.

2. The composition of claim 1 wherein the composition comprises from about 0.1% to about 10%, by weight of the composition, of the UVA-absorbing dibenzoylmethane sunscreen active.

3. The composition of claim 1 wherein the composition comprises from about 0.2% to about 7%, by weight of the composition, of the UVA-absorbing dibenzoylmethane sunscreen active.

4. The composition of claim 1 wherein the composition comprises from about 0.4% to about 5%, by weight of the composition, of the UVA-absorbing dibenzoylmethane sunscreen active.

5. The composition of claim 1 wherein the UVA-absorbing dibenzoylmethane sunscreen active is selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4'tert-butyl-4'methoxydibenzoylmethane, and mixtures thereof.

6. The composition of claim 1 wherein the UVA-absorbing dibenzoylmethane sunscreen active is selected from the group consisting of 4-(1,1-dimethylethyl)-4'methoxydibenzoylmethane, 4-isopropyldibenzoylmethane, and mixtures thereof.

7. The composition of claim 1 wherein the composition comprises from about 0.1% to about 6%, by weight of the composition, of the stabilizing agent.

8. The composition of claim 1 wherein composition comprises from about 0.3% to about 3%, by weight of the composition, of the stabilizing agent.

9. The composition of claim 1 wherein the stabilizing agent is selected from the group consisting of 2-ethylhexyl-2-cyano-3,3-diphenylacrylate, ethyl-2-cyano-3,3-diphenylacrylate, 2-ethylhexyl-3,3-diphenylacrylate, ethyl-3,3-bis(4-methoxyphenyl) acrylate, and mixtures thereof.

10. The composition of claim 1 wherein the mole ratio of the stabilizing agent to the UVA-absorbing dibenzoylmethane sunscreen active is less than about 0.75.

11. The composition of claim 1 wherein the mole ratio of the stabilizing agent to the UVA-absorbing dibenzoylmethane sunscreen active is less than about 0.65.

12. The composition of claim 1 wherein the UVB sunscreen active is 2-phenyl-benzimidazole-5-sulfonic acid.

13. The composition of claim 12 wherein the composition comprises from about 0.1% to about 4%, by weight of the composition, of 2-phenyl-benzimidazole-5-sulfonic acid.

14. The composition of claim 13 wherein the composition comprises from about 0.5% to about 2.5%, by weight of the composition, of 2-phenyl-benzimidazole-5-sulfonic acid.

15. The composition of claim 1 wherein the UVB sunscreen active is a physical inorganic sunblock selected from the group consisting of zinc oxide, titanium dioxide, and mixtures thereof.

16. The composition of claim 1 wherein the composition comprises:

a) from about 0.1% to about 10%, by weight of the composition, of a UVA-absorbing dibenzoylmethane sunscreen active selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4'tert-butyl-4'methoxydibenzoylmethane, and mixtures thereof;

b) from about 0.1% to about 6%, by weight of the composition, of a stabilizing agent selected from the group consisting of 2-ethylhexyl-2-cyano-3,3-diphenylacrylate, ethyl-2-cyano-3,3-diphenylacrylate, 2-ethylhexyl-3,3-diphenylacrylate, ethyl-3,3-bis(4-methoxyphenyl)acrylate, and mixtures thereof;

c) a safe and effective amount of a UVB sunscreen active selected from the group consisting of 2-phenyl-benzimidazole-5-sulfonic acid, TEA salicylate, octyl dimethyl PABA, zinc oxide, titanium dioxide, and mixtures thereof, provided that the composition comprises less than or equal to about 5% inorganic physical sunblock; and d) a carrier suitable for application to the skin;

wherein the mole ratio of the stabilizing agent to the UVA-absorbing dibenzoylmethane sunscreen active is less than 0.8 and wherein the composition is substantially free of benzylidene camphor derivatives.

17. A composition suitable for use as sunscreen comprising:

a) from about 0.1% to about 10%, by weight of the composition, of a UVA-absorbing dibenzoylmethane sunscreen active;

b) from about 0.1% to about 6%, by weight of the composition, of a stabilizing agent having the formula

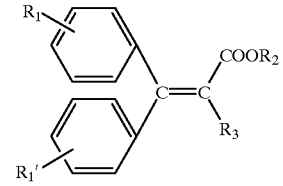

wherein $R_1$ and $R_1'$ are independently in the para or meta position and are independently a hydrogen atom or a straight- or branched chain $C_1$–$C_8$ alkyl radical, $R_2$ is a straight- or branched-chain $C_1$–$C_{12}$ alkyl radical; and $R_3$ is a hydrogen atom or a —CN radical;

c) from about 0.1% to about 10%, by weight of the composition, of 2-phenyl-benzimidazole-5-sulfonic acid; and d) a carrier suitable for application to the skin;

wherein the mole ratio of the stabilizing agent to the UVA-absorbing dibenzoylmethane sunscreen active is less than 0.8 and wherein the composition is substantially free of benzylidene camphor derivatives.

18. The composition of claim 17 wherein the UVA-absorbing dibenzoylmethane sunscreen active is selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4'tert-butyl-4'methoxydibenzoylmethane, and mixtures thereof.

19. A composition suitable for use as sunscreen comprising:

a) from about 2% to about 3%, by weight of the composition, of a UVA-absorbing dibenzoylmethane sunscreen active selected from the group consisting of 4-isopropyldibenzoylmethane, 4-(1,1-dimethylethyl)-4'methoxydibenzoylmethane, and mixtures thereof;

b) from about 1.5% to about 2.25%, by weight of the composition, of a stabilizing agent selected from the group consisting of 2-ethylhexyl-2-cyano-3,3-diphenylacrylate, ethyl-2-cyano-3,3-diphenylacrylate, 2-ethylhexyl-3,3-diphenylacrylate, ethyl-3,3-bis(4-methoxyphenyl)acrylate, and mixtures thereof;

c) from about 1.0% to about 1.5%, by weight of the composition, of 2-phenyl-benzimidazole-5-sulfonic acid; and d) a carrier suitable for application to the skin;

wherein the mole ratio of the stabilizing agent to the UVA-absorbing dibenzoylmethane sunscreen active is less than about 0.65.

* * * * *